United States Patent
Dube et al.

(10) Patent No.: US 10,281,388 B2
(45) Date of Patent: May 7, 2019

(54) TESTER TO ESTIMATE CO-EFFICIENT OF FRICTION AND DETERMINE PROPERTIES OF A SAMPLE LUBRICANT

(71) Applicant: Ducom Instruments Pvt. Ltd., Bangalore, Karnataka (IN)

(72) Inventors: Narendra Mohan Dube, Karnataka (IN); Anshuman Dube, Karnataka (IN); Amit Ganguli, Karnataka (IN); B. S. Parameshwara, Karnataka (IN)

(73) Assignee: DUCOM INSTRUMENTS PVT. LTD. (IN)

(*) Notice: Subject to any disclaimer, the term of this patent is extended or adjusted under 35 U.S.C. 154(b) by 190 days.

(21) Appl. No.: 15/383,655

(22) Filed: Dec. 19, 2016

(65) Prior Publication Data

US 2017/0176319 A1    Jun. 22, 2017

(30) Foreign Application Priority Data

Dec. 18, 2015   (IN) ........................... 6774/CHE/2015

(51) Int. Cl.
*G01N 19/02* (2006.01)
*G01N 3/56* (2006.01)
*G01N 33/28* (2006.01)

(52) U.S. Cl.
CPC .............. *G01N 19/02* (2013.01); *G01N 3/56* (2013.01); *G01N 33/2888* (2013.01)

(58) Field of Classification Search
CPC ...... G01N 3/56; G01N 19/02; G01N 33/2888; G01N 33/30; F16N 2250/42
USPC ................................ 73/9, 10, 53.05; 184/7.4
See application file for complete search history.

(56) References Cited

U.S. PATENT DOCUMENTS

| 1,716,393 | A |   | 6/1929 | Thompson |
|-----------|---|---|--------|----------|
| 3,939,690 | A | * | 2/1976 | Kuss ........................ G01N 3/56 73/9 |
| 2003/0101793 | A1 |   | 6/2003 | Evans |

FOREIGN PATENT DOCUMENTS

| CN | 2042197   | 8/1989  |
| CN | 2081534   | 7/1991  |
| CN | 101551315 | 10/2009 |
| CN | 101629888 | 1/2010  |
| CN | 102564882 | 7/2012  |
| CN | 102564882 A | 7/2012 |
| CN | 103901184 | 7/2014  |
| CN | 104198100 | 12/2014 |
| CN | 204203063 | 3/2015  |
| CN | 104634731 | 5/2015  |

(Continued)

*Primary Examiner* — Benjamin R Schmitt
(74) *Attorney, Agent, or Firm* — Gearhart Law, LLC (57) ABSTRACT

A tester to estimate co-efficient of friction and determine other properties of a sample lubricant is disclosed. The tester includes a base structure mounted on a compound bearing and a ballpot located on the base structure. The ballpot carries at least three non-rotating balls. Further, the tester includes a bi-direction rotatable motor with a rotatable shaft having a rotating ball. In addition, the tester includes a loading system to load the non-rotating balls against the rotating ball. A load sensor connected to the loading system measures applied load. Furthermore, the tester includes at least one load cell provided in communication with the ballpot to provide at least one output signal. The output signal received from the load cell and the load sensor is recorded and processed in a data acquisition and control system.

8 Claims, 5 Drawing Sheets

(56) References Cited

FOREIGN PATENT DOCUMENTS

| | | |
|---|---:|---:|
| CN | 204346854 | 5/2015 |
| CN | 204422389 | 6/2015 |
| CN | 204613051 | 9/2015 |
| CN | 204784517 | 11/2015 |
| CN | 204832968 | 12/2015 |
| CN | 105352834 | 2/2016 |
| CN | 205027623 | 2/2016 |
| CN | 205138693 | 4/2016 |
| CN | 205138694 | 4/2016 |
| CN | 205720224 | 11/2016 |
| CN | 206146769 | 5/2017 |
| CN | 106872351 | 6/2017 |
| DE | 19921760 | 11/2000 |
| DE | 102006022349 | 11/2007 |
| DE | 102014103231 | 9/2015 |
| DE | 102014008127 | 12/2015 |
| FR | 2907903 | 5/2008 |
| GB | 1366303 | 9/1974 |
| GB | 1366303 A | 9/1974 |
| NL | 7811870 | 6/1979 |
| RU | 2075055 | 3/1977 |
| RU | 57908 | 10/2006 |
| RU | 94343 | 9/2010 |
| RU | 94343 U1 | 9/2010 |
| RU | 135418 | 12/2013 |
| SU | 970190 | 10/1982 |
| SU | 1133500 | 1/1985 |
| SU | 1559293 | 4/1990 |
| SU | 1589130 | 8/1990 |
| WO | 2008050015 | 5/2008 |
| WO | 2008080015 A1 | 5/2008 |

\* cited by examiner

TESTER TO ESTIMATE CO-EFFICIENT OF FRICTION AND DETERMINE PROPERTIES OF A SAMPLE LUBRICANT

CLAIM OF PRIORITY

This application claims priority to Indian Application No. 6774/CHE/2015 filed on Dec. 18, 2015, the entire disclosures of which is incorporated herein by reference.

FIELD OF THE EMBODIMENTS

The embodiments herein relate generally to a four ball tester to apply load and measure parameters such as but not limited to, wear-preventive, extreme pressure, frictional torque, fatigue, shear stability behavior and to estimate co-efficient of friction of any sample lubricant. More particularly, the embodiments herein relates to the four-ball tester capable of applying multiple range of loads in a controlled manner, rotating in two directions (i.e. clockwise and counter clockwise) in a controlled manner and measure the abovementioned parameters. Thus eliminating the need for two different machines to conduct wear preventive and extreme pressure tests so as to meet requirements of ASTM D 2266, ASTM D 2783, ASTM D 2596, ASTM D 5183, ASTM D 4172, and ASTM D 3702.

BACKGROUND OF THE EMBODIMENTS

Conventionally, Four-ball tester includes a ballpot with three steel balls of ½ inch diameter positioned inside the ballpot. The steel balls are held very tightly together by a conical ring that is secured with a lock nut to hold balls in place. A test lubricant is filled in the ballpot submerging the three balls. The four-ball tester includes a heater block to heat the test lubricant to a predetermined test temperature. Further, a bearing supports the ballpot from the bottom. Three balls in the ballpot are forced against a fourth ball held in a collet attached to a spindle which is in-turn connected to an electric motor. The force between the lower three balls and the upper fourth ball may be measured using a load cell to ensure that load is within the specified range depending on test procedure. Upon rotation of the top ball, a force is transmitted to the test balls in the ballpot, tending to rotate the ballpot. A torque sensor is operably connected to the ballpot which prevents its rotation due to friction torque, thereby measuring frictional torque as reaction.

In wear preventive test, the fourth top ball is rotated against the three balls in the ballpot for a predetermined time period. At the end of the test the motor is stopped, the load is removed, and the ballpot is taken off the tester. The lubricant in the ballpot is drained. The ballpot with the three balls still locked in place is kept under a microscope to measure the size of wear scars. The wear scars result from the top ball rotating against each of the bottom three balls under the test load. The wear scars are measured for each of the bottom three balls. In general, each of the three bottom balls will have a wear scar that is very similar in size and shape. A measurement is made with a microscope of each wear scar diameter, along the major and minor diameters. A total of six measurements are taken, two for each ball, and then the average of the six readings is considered to be the wear scar diameter for a given test fluid under a specific test method.

For extreme pressure test, the fourth top ball is rotated against the three balls in the ballpot for a predetermined time by constantly increasing the load in predetermined steps. At the end of the test, the balls weld to each other and the motor ceases. Once welding has occurred the load is removed, and the balls are taken out of the tester. The load before the weld and at the point of weld are analyzed to measure the extreme pressure test parameters.

However, existing four-ball tester has numerous drawbacks. The main drawback in the conventional machines is that each four ball tester is manufactured to perform only one type of specific test. For example, when a wear preventive test is conducted, the tester is operated for 392 N while for an extreme pressure test, the tester is operated up to 800 kgf (7846 N). Further, no means is provided to directly measure the exact actual load on the test balls. The load cell for wear preventive test and extreme pressure test will have accuracy not more than 0.1%. Therefore to meet the requirements of ASTM, two different testers are manufactured. This leads to additional expenses in manufacturing and maintaining.

Thus, there exists a need for a four ball tester having a high sensitivity needed to apply a test load of 392 N with variation not more than 2 N, and capable of applying test loads up to 800 kgf. Thus eliminating the need for two different machines to conduct wear preventive test and extreme pressure test so as to meet requirements of ASTM D2266, ASTM D 2783, ASTM D 2596, ASTM D 5183, ASTM D 4172, and ASTM D 3702.

SUMMARY OF THE EMBODIMENTS

A tester to estimate co-efficient of friction and determine other properties of a sample lubricant includes a base structure mounted on at least one compound bearing. Further, the tester includes a ballpot placed on the base structure. The ballpot carries plurality of non-rotating balls. Furthermore, the tester includes a bi-direction rotatable motor with a rotatable shaft. A rotating ball is provided at one end of the shaft. In addition, the tester includes a loading system to load the non-rotating balls against the rotating ball. A load sensor is connected to the loading system to measure applied load. Moreover, the tester includes at least one load cell provided in communication with the ballpot to provide at least one output signal. The output signal received from the load cell and the load sensor is recorded and processed in a data acquisition and control system.

The primary object of the embodiments herein is to provide a four-ball tester to, apply multiple range of loads in a controlled manner, capable of rotating in two directions (i.e. clockwise and counter clockwise) in a controlled manner and measure parameters such as but not limited to, wear-preventive, extreme pressure, frictional torque, fatigue, shear stability behavior and to estimate co-efficient of friction of any sample lubricant and frictional torque in multiple range.

Another object of the embodiments herein is to provide a four ball tester to conduct both wear preventive and extreme pressure tests in single machine so as to meet requirements of ASTM D2266, ASTM D 2783, ASTM D 2596, ASTM D 5183, ASTM D 4172, and ASTM D 3702.

Also another object of the embodiments herein is to provide a first frictional torque load cell having high sensitivity commensurate with frictional torque in wear preventive test operably connected to a ballpot supported by a low friction rotary element bearing or a frictionless hydrostatic bearing or an aerostatic bearing to provide an output signal indicative of first frictional torque.

Still another object of the embodiments herein is to provide a second frictional torque load cell having high capacity commensurate with peak torque generated when balls weld in extreme pressure test is operably connected to the ballpot supported by a rolling element thrust bearing to provide an output signal indicative of second frictional torque.

Also another object of the embodiments herein is to provide a tester to apply load in a controlled manner and continuously measure the accurate applied load.

Still another object of the embodiments herein is to provide a bi-directional rotatable motor with controllable speed and acceleration.

Still another object of the embodiments herein is to provide a data acquisition and control system to measure, record and control the operating parameters, to determine at least one of wear-preventive, extreme pressure, frictional torque, fatigue, shear stability behavior and to estimate co-efficient of friction of any sample lubricant and frictional torque in multiple range.

These and other objects of the embodiments herein shall be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

An exemplary embodiment is illustrated in the accompanying drawings, throughout which like reference letters indicate corresponding parts in the various figures. The exemplary embodiments herein will be better understood from the following description with reference to the drawings, in which.

DESCRIPTION OF THE PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve four-ball tester to apply multiple range of loads in a controlled manner, capable of rotating in two directions (i.e. clockwise and counter clockwise) in a controlled manner and measure parameters such as but not limited to, wear-preventive, extreme pressure, frictional torque, fatigue, shear stability behavior and to estimate co-efficient of friction of any sample lubricant and frictional torque in multiple range. Further, the embodiments herein achieve the tester 100 to conduct wear preventive and extreme pressure tests so as to meet requirements of ASTM D2266, ASTM D 2783, ASTM D 2596, ASTM D 5183, ASTM D 4172, and ASTM D 3702. Furthermore, the embodiments herein achieve the tester provided in communication with a data acquisition and control system configured to directly measure the load and frictional torque during its operation, and to provide output signal corresponding to the operating conditions. Referring to the drawings, and more to FIGS. 1 to 5, where similar reference characters denote corresponding features consistently throughout the figures, we now describe the embodiments.

As used herein, the term compound bearing refers to combination of bearing selected from a combination of aerostatic thrust bearing with a rolling element thrust bearing or a frictionless hydrostatic bearing with a rolling element thrust bearing. Further, the term plurality of sensors refers to plurality of sensors configured to measure multiple properties of a test lubricant. The plurality of sensors includes load cell, temperature sensor, friction sensor, torque sensor etc. Furthermore at many instance, upper ball is referred as rotating ball and the lower balls is referred as stationary balls lower test balls or non-rotating balls. Also, at few instances the term lubricant is referred as sample lubricant or test lubricant.

The four ball tester 100 according to an embodiment disclosed, includes a compound bearing 101, a base structure 103, a ballpot 105, a lock nut 107, at least three non-rotating balls 109, at least one rotating ball 111, a collet 113, a rotatable shaft 115, a loading system 117, a heater 119, a plurality of sensors 121, a controller 123 (not shown in figs), and a data acquisition and control system 125 (not shown in figs), plurality of pockets 127, a first frictional torque load cell 129, a second frictional torque load cell 131, a bi-direction rotatable motor 133, a load sensor 135 (not shown in figs), and a conical ring 137.

In one embodiment, the compound bearing 101 is manufactured by combining at least two bearings i.e. an aerostatic bearing with a rolling element thrust bearing or a frictionless hydrostatic bearing with a rolling element thrust bearing, for independent angular mobility of the ballpot 105. It should be noted that the compound bearing 101 described herein is merely for an exemplary embodiment, however the tester 100 can include other types of bearing.

In one embodiment, the fourball tester 100 includes the aerostatic bearing or hydrostatic bearing which in turn utilizes a thin film of high-pressure air or fluid to support the ballpot 105. A plurality of pockets 127 are provided on the surface of the aerostatic bearing to pass the high-pressure air or fluid. During the test, the air or fluid passed through the pockets 127 is recirculated for the entire period of test. Further, the lower part of the aerostatic bearing is assembled with the rolling element thrust bearing, thus facilitating in independent angular mobility of the ballpot 105.

In one embodiment, the fourball tester 100 includes the base structure 103 mounted on the compound bearing. The ballpot 105 is placed above the base structure 103. The ballpot 105 is fabricated in shape of a cup, in which it can accommodate three steel balls of ½ inch diameter. During test, a test lubricant is filled in the ballpot 105 submerging the three non-rotating balls 109.

In one embodiment, the lower three balls along with the test lubricant is firmly held in the ballpot 105. The lock nut 107 is threaded onto the ballpot 105 against the conical ring 137 to secure the lower balls 109 in the ballpot 105. The conical ring 137 tightly clamps the lower balls 109 against lower surface of the ballpot 105. This clamping action prevents movement of the lower test balls 109 within the ballpot 105 so that only sliding contact occurs between the upper ball 111 and the lower balls 109. The measurements obtained during the test are very accurate as the entire load is supported by the contact of the lower balls 109 on the upper ball 111, and there is no additional friction. In one embodiment, additional instruments or other connections can be used along with the ballpot 105 itself without causing any errors that would occur in existing ballpot designs.

In one embodiment, the four ball tester 100 includes the heater 119 provided in the ballpot 105. The heater 119 is electrically connected to the controller 123 to control the temperature of the lubricant. In one embodiment, the controller 123 aids in heating the sample lubricant, and maintaining the lubricant temperature at a desired level during the test. The heater 119 may be supported with insulating pad in the ballpot 105.

It should be noted that the aforementioned ballpot 105 is provided for ease of understanding of the embodiment. However, certain other embodiments may have a different configurations of the ballpot 105 and certain other embodiments may be included or excluded without otherwise deterring the intended function of the ballpot 105 as is apparent from this description and drawings are also within the scope of the embodiment as disclosed.

Figure 1:
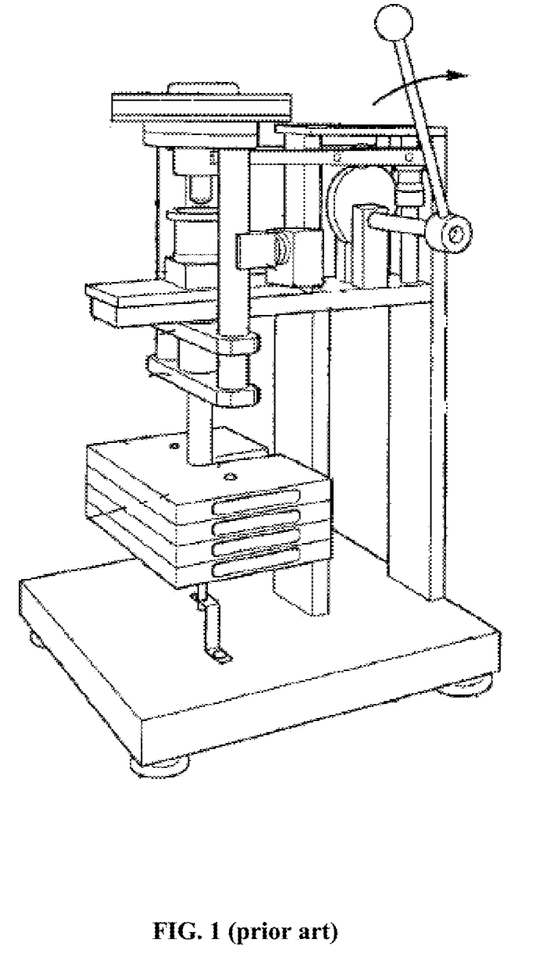
FIG. 1 is a schematic side elevational view of a prior art four-ball tester including a lever arm for generating a test load.
Figure 2:
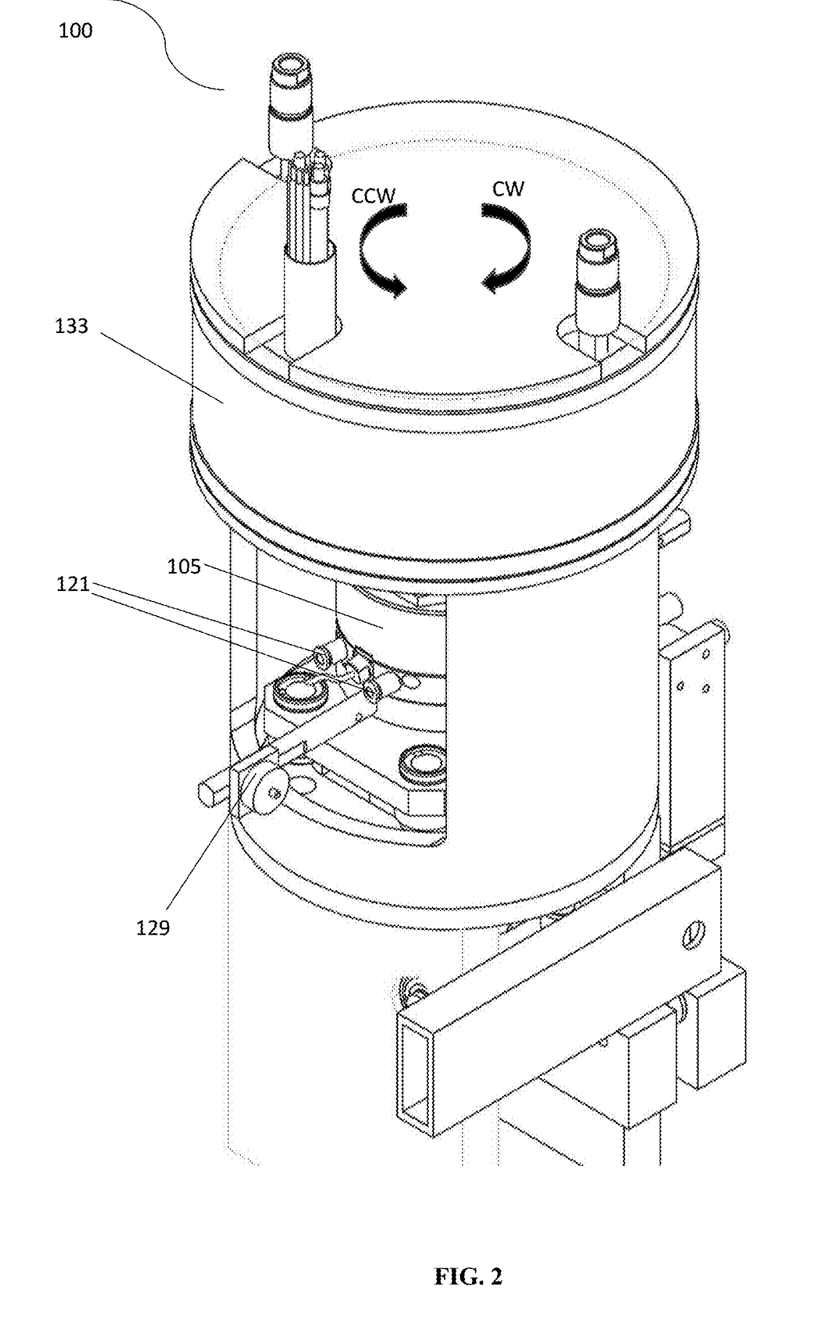
FIG. 2 illustrates a perspective view of a four ball tester according to an embodiment as disclosed.
Figure 3:
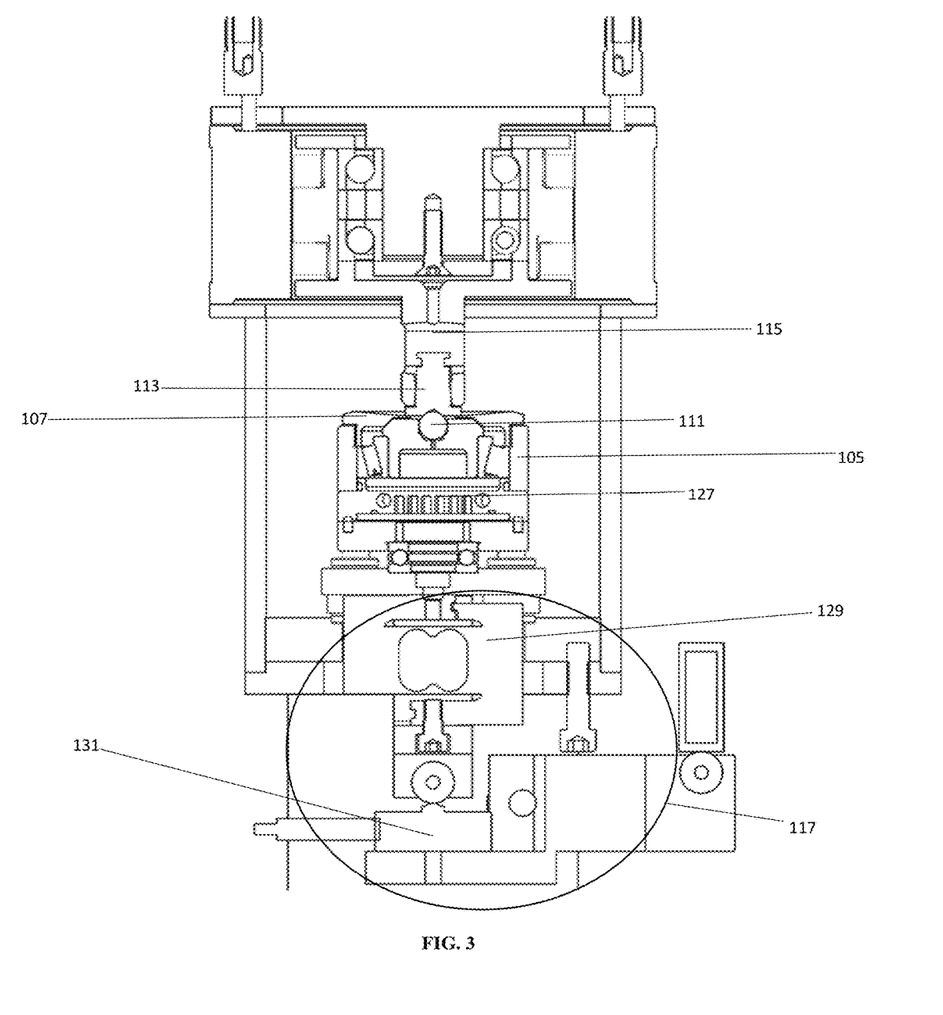
FIG. 3 illustrates a sectional front view of a four ball tester according to an embodiment as disclosed.
Figure 4:
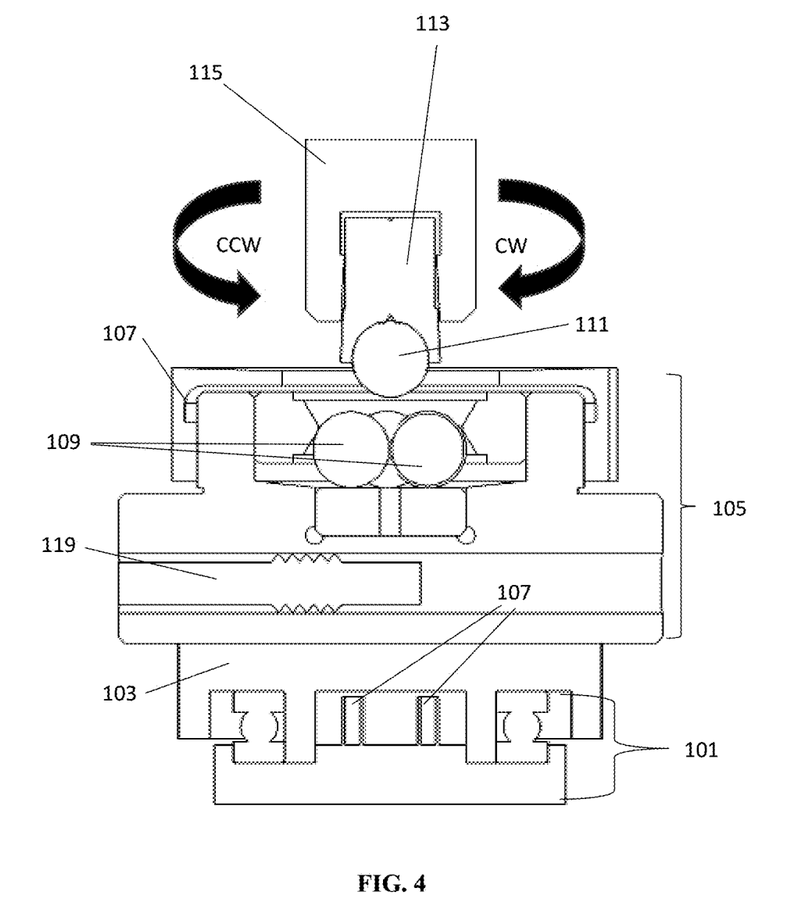
FIG. 4 illustrates an enlarged a sectional view of an arrangement of ballpot and collet in the four ball tester according to an embodiment as disclosed.
Figure 5:
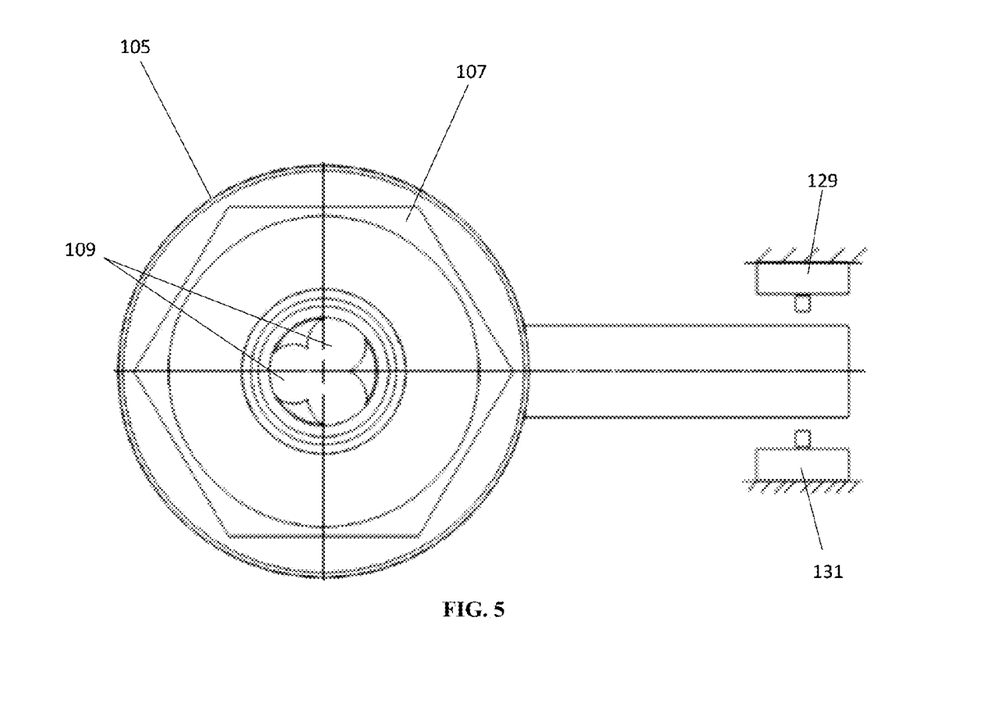
FIG. 5 illustrates a top view of a ballpot according to an embodiment as disclosed.

In one embodiment, the rotatable shaft 115 is operatively coupled to a bi-directional rotatable electric motor for rotation as indicated in FIG. 2. In one embodiment, the bi-direction rotatable shaft 115 is rotated in either one of clockwise or counter clockwise. For example, when the fourball tester 100 is operated for a wear preventive test, the bi-directional rotatable motor 133 rotates in clockwise direction. The first frictional torque load cell 129 operably connected to the ballpot 105, measures the first frictional torque between the lower balls 109 and the upper ball 111. Similarly when the fourball tester 100 is operated for the extreme pressure test, the bi-directional rotatable motor 133 is rotated in counter clockwise and the second frictional torque load cell 131 operably connected to the ballpot, measures the second frictional torque between the lower balls 109 and the upper ball 111.

It should be noted that the aforementioned bi-direction rotatable shaft 115 is provided for ease of understanding of the embodiment. However, certain other embodiments may have a different configurations of the bi-direction rotatable shaft 115 and certain other embodiments may be included or excluded without otherwise deterring the intended function of the bi-direction rotatable shaft 115 as is apparent from this description and drawings are also within the scope of the embodiment as disclosed.

The four-ball tester 100 ensures that all frictional forces measured by the load cells are due to the frictional engagement between the upper test ball 111 and the lower test balls 109, and eliminates potential errors caused by thrust bearings or the like present in prior four-ball test arrangements.

In one embodiment, the tester 100 includes the first frictional torque load cell 129 operably connected to the ballpot 105. The first frictional torque load cell 129 is a low capacity and high sensitivity load cell having sensitivity proportional or more then the frictional torque in the wear preventive test. During the wear preventive test the ballpot 105 is supported on a frictionless hydrostatic bearing or an aerostatic bearing. An output signal indicative of the first frictional torque is generated by the first frictional torque load cell 129. The output signal is acquired and processed in the data acquisition and control system 125. The first frictional torque load cell 129 measures a low load of 50 kg or 500 N.

In one embodiment, the tester 100 includes the second frictional torque load cell 131 operably connected to the ballpot 105. The second frictional torque load cell 131 is a high capacity load cell having capacity proportional or more then the peak torque in the extreme pressure test. During the extreme pressure test the bi-direction rotatable shaft 115 is rotated in counter clockwise and the ballpot 105 is supported on the rolling element thrust bearing. An output signal indicative of the second frictional torque is generated by the second frictional torque load cell 131. The output signal is acquired and processed by the data acquisition and control system 125. The second load cell 131 measures a high load up to 800 kg. The second torque load cell 131 holds high capacity which is proportional to a peak torque generated when balls weld in an extreme pressure test to de-energize the motor if it exceeds a predetermined limit.

It should be noted that the aforementioned first frictional torque load cell 129 and second frictional torque load cell 131 is provided for ease of understanding of the embodiment. However, certain other embodiments may have a different configurations of the frictional torque load cell and certain other embodiments may be included or excluded without otherwise deterring the intended function of the frictional torque load cell as is apparent from this description and drawings are also within the scope of the embodiment as disclosed.

In one embodiment, a belt and pulley arrangement is used for rotating the bi-direction rotatable shaft 115. The collet 113 of the four ball tester 100 includes an inner surface having a shallow taper that engages the upper ball 111. The tapered portion tightly contacts the outer surface of the upper ball 111 and holds the ball in the collet 113. The contact forces are sufficient to ensure that the ball does not slip in collet 113 during testing. In general, any taper angle that provides sufficient friction to prevent rotation of the upper ball 111 in the collet 113 is suitable. In a preferred embodiment, the collet 113 is made of a material that is different from the material of the upper ball 111 to prevent welding between the upper ball 111 and the collet 113. The materials include aluminum, bronze, amaloy or other such materials. The collet 113 can be utilized for both type of testing i.e. for the wear preventive test, and the extreme pressure test.

It should be noted that the aforementioned collet 113 is provided for ease of understanding of the embodiment. However, certain other embodiments may have a different configuration of the collet 113 without otherwise deterring the intended function of the collet 113 as is apparent from this description and drawings are also within the scope of the embodiment as disclosed.

In one embodiment, the loading system 117 of the four ball tester 100 is selected from a group consisting of pneumatic loading, hydraulic loading, and manual loading (dead weights). The loading system 117 imparts normal load between the lower balls 109 and the upper ball 111 during the test. In one embodiment, the loading system 117 provided in the four ball tester 100 is configured to apply constant and varying loads during the test. The range of loading varies from 1 kg to 1000 kg. For example, when the wear preventive test is performed using the tester 100, the load sensor 135 connected in the load path measures constant low loads applied by the loading system 117. Similarly, when the extreme pressure test is performed using the tester 100, the load sensor 135 connected in the load path measures the varying high loads applied by the loading system 117.

In one embodiment, the four ball tester 100 includes at least one load sensor 135 to continuously measure normal load applied by the loading system 117 during the test. Further, the measured normal load is processed by the data acquisition and control system 125 to control the load applied on the upper ball 111.

In one embodiment, the four ball tester 100 is connected to a data acquisition and control system 125 which is programmed to provide both variable load profiles and constant load profiles with controllable loading rate during a test. For example, when an extreme pressure test is performed in the tester 100, the data acquisition and control system 125 can be programmed to provide a reference signal that increases the load at a controlled rate during the test until the rotation of the balls ceases. Alternately, the data acquisition and control system 125 can be programmed to provide constant load profiles for the wear preventive test. The data acquisition and control system 125 further receives output signals indicative of speed of the rotation of the upper ball 111 and temperature of the heater 119 or lubricant under test, from a speed sensor and a temperature sensor.

In one embodiment, the four ball tester 100 includes plurality of sensors. The plurality of sensors are selected from a group consisting of load sensor 135, temperature sensor, pressure sensor, and torque sensor (load cell). The outputs of the plurality of sensors are received as input by the data acquisition and control system 125 and an output signal corresponding to the operating conditions is displayed.

It should be noted that the aforementioned sensors are provided for ease of understanding of the embodiment. However, certain other embodiments may have a different sensors and certain other embodiments may be included or excluded without otherwise deterring the intended function of the sensor as is apparent from this description and drawings are also within the scope of the embodiment as disclosed.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

What is claimed is:

1. A tester to determine properties of a sample or test lubricant, said tester comprising:
    a base structure mounted on a compound bearing, wherein the compound bearing is selected from a group consisting of an aerostatic bearing combined with a rolling element thrust bearing, and a frictionless hydrostatic bearing combined with the rolling element thrust bearing;
    a ballpot supported on the base structure, wherein the ballpot carries a plurality of non-rotating balls;
    a motor to rotate a shaft having at least one rotating ball held in contact with the plurality of non-rotating balls, wherein the motor coupled to the rotatable shaft is a bi-directional variable speed motor;
    a loading system to load the plurality of non-rotating balls against the at least one rotating ball;
    a load sensor provided in communication with the loading system to measure the applied load; and
    at least one first load cell and at least one second load cell provided in communication with the ballpot to measure and provide at least one first output signal and at least one second output signal.

2. The tester as claimed in claim 1, wherein the ballpot is supported on the frictionless hydrostatic bearing and the aerostatic bearing, and rotated clockwise to provide an output signal indicative of a first frictional torque measured by the at least one first load cell in a wear preventive test.

3. The tester as claimed in claim 1, wherein the ballpot is supported on the rolling element thrust bearing, and rotated in counter clockwise to provide an output signal indicative of a second frictional torque measured by the at least one second load cell in an extreme pressure test.

4. The tester as claimed in claim 1, wherein the tester comprises a plurality of sensors selected from a group consisting of a wear sensor, a load sensor, a temperature sensor, and a friction torque sensor.

5. The tester as claimed in claim 1, wherein the loading system is selected from a group consisting of a hydraulic loading system, a pneumatic loading system, a dead weight loading system, and a motorised loading.

6. The tester as claimed in claim 1, wherein the tester is integrated with a data acquisition and control system to acquire and process the output signals from the at least one first load cell, the at least one second load cell, and a plurality of sensors to determine at least one of torque, wear preventive, extreme pressure, frictional, fatigue and shear stability behavior of lubricants.

7. The tester as claimed in claim 6, wherein the data acquisition and control system includes a controller to perform at least one of controlling acceleration of the motor, controlling loading rate applied before the motor starts rotating, and controlling the loading rate synchronized in a pre-determined manner to motor rotation.

8. A method to determine properties of a sample or test lubricant, the method comprising:
    mounting a base structure on at least one compound bearing, wherein the compound bearing is selected from a group consisting of an aerostatic bearing combined with a rolling element thrust bearing, and a frictionless hydrostatic bearing combined with the rolling element thrust bearing;
    supporting a ballpot on the base structure, wherein the ballpot carries a plurality of non-rotating balls;
    providing a motor to rotate a shaft having at least one rotating ball held in contact with the plurality of non-rotating balls, wherein the motor coupled to the rotatable shaft is a bi-directional variable speed motor;
    providing a loading system to load the plurality of non-rotating balls against the at least one rotating ball;
    providing a load sensor in communication with the loading system to measure the applied load;

providing at least one first load cell and at least one second load cell in communication with the ballpot; and measuring and recording at least one first output signal and at least one second output signal from the at least one first load cell and the at least one second load cell.

\* \* \* \* \*